United States Patent
Santos Garcia et al.

(10) Patent No.: US 11,937,625 B2
(45) Date of Patent: Mar. 26, 2024

(54) ORAL ADMINISTRATION FORMULATION OF BLUEBERRY EXTRACT AS A COADJUVANT FOR PRESERVING THE HEALTH OF HUMAN PRECORNEAL FILM

(71) Applicant: CENTRO DE RETINA MEDICA Y QUIRURGICA, S.C., Zapopan (MX)

(72) Inventors: Arturo Santos Garcia, Zapopan (MX); Juan Carlos Altamirano Vallejo, Zapopan (MX); Jose Alonso Chavez Garcia, Zapopan (MX); Alejandro Gonzalez De La Rosa, Zapopan (MX)

(*) Notice: Subject to any disclaimer, the term of this patent is extended or adjusted under 35 U.S.C. 154(b) by 223 days.

(21) Appl. No.: 16/954,401

(22) PCT Filed: Dec. 18, 2018

(86) PCT No.: PCT/MX2018/000154
§ 371 (c)(1),
(2) Date: Jun. 16, 2020

(87) PCT Pub. No.: WO2019/125127
PCT Pub. Date: Jun. 27, 2019

(65) Prior Publication Data
US 2021/0076726 A1    Mar. 18, 2021

(30) Foreign Application Priority Data
Dec. 20, 2017   (MX) .................. MX/A/2017/016991

(51) Int. Cl.
A23L 33/19     (2016.01)
A23L 33/105    (2016.01)
A23L 33/12     (2016.01)
A23L 33/155    (2016.01)

(52) U.S. Cl.
CPC ............. *A23L 33/19* (2016.08); *A23L 33/105* (2016.08); *A23L 33/12* (2016.08); *A23L 33/155* (2016.08)

(58) Field of Classification Search
None
See application file for complete search history.

(56) References Cited

U.S. PATENT DOCUMENTS

| | | | |
|---|---|---|---|
| 2002/0095000 A1 | 7/2002 | Troyer et al. | |
| 2003/0203962 A1* | 10/2003 | Howell ...................... | A23L 2/02 549/406 |
| 2006/0263455 A1* | 11/2006 | Anton ..................... | A61K 36/45 514/23 |
| 2008/0161234 A1* | 7/2008 | Andersch ................ | A61P 15/02 514/2.7 |
| 2011/0009313 A1* | 1/2011 | Sato ......................... | A61P 31/00 514/19.3 |
| 2011/0280851 A1* | 11/2011 | Herzlinger ............. | A61K 33/04 424/94.1 |

FOREIGN PATENT DOCUMENTS

| | | | |
|---|---|---|---|
| CN | 102379446 A | 3/2012 | |
| CN | 105029443 A | 11/2015 | |
| EP | 0655241 A1 * | 5/1995 | ............... A61K 9/48 |
| WO | 2004006801 A2 | 1/2004 | |
| WO | WO-2008018111 A2 * | 2/2008 | ............. A61K 36/45 |

OTHER PUBLICATIONS

Bausch + Lomb "Ocuvite Eye Vitamin and Mineral Supplements with Lutein." Bausch Lomb, Jun. 22, 2020, Downloaded from the internet from https://www.bausch.com/ecp/our-products/eye-vitamins/general-eye-health-vitamins/ocuvite-eye-vitamin-and-mineral-supplements-with-lutein on Jun. 18, 2020 (4 pages).

Creuzot, C., et al. "Improvement of dry eye symptoms with polyunsaturated fatty acids." Journal francais d'ophtalmologie 29.8 (2006): 868. [English Abstract].

Devendra, Jaya, and Sneha Singh. "Effect of oral lactoferrin on cataract surgery induced dry eye: a randomised controlled trial." Journal of clinical and diagnostic research: JCDR 9.10 (2015): NC06.

Diabitam,."Diabitam" PLM, Sep. 14, 2018, Downloaded from the internet from https://www.medicamentosplm.com/Home/productos/diabitam_capsulas/88/101/7241/14 on Jun. 26, 2020. (16 pages).

ISA/MX, International Search Report and Written Opinion (with English translation of ISR), dated May 10, 2019, re PCT International Patent Application No. PCT/mx2018/000154.

Nojima, Yasuhiro, et al. "Development of poly (ethylene glycol) conjugated lactoferrin for oral administration." Bioconjugate chemistry 19.11 (2008): 2253-2259.

(Continued)

*Primary Examiner* — Dale R Miller
(74) *Attorney, Agent, or Firm* — Feeney IP Law; Alan F. Feeney; Daniel Sullivan

(57) ABSTRACT

The invention relates to a nutraceutical formulation of blueberry extract, fish oil (omega-3 and omega-6), recombinant human lactoferrin, vitamin A and vitamin E, for human oral consumption. The invention belongs to the field of ophthalmology and has been developed as a coadjuvant for preserving the health of the precorneal film and of the eye surface. This formulation contains an extract of natural origin (*Vaccinium myrtillus* L) with antioxidant and anti-inflammatory properties; it also uses eicosapentaenoic acid (EPA), omega-6, and docosahexaenoic acid (DHA), omega-3, obtained from fish oil and which, together with lactoferrin, vitamin A and vitamin E, improves tear quality, since these compounds have anti-microbial and anti-inflammatory effects. This formulation has been designed as a coadjuvant for preserving the health of the precorneal film. No formulation for oral administration of a blueberry extract together with lactoferrin, in combination with vitamin A, vitamin E and fish oil (eicosapentaenoic acid and docosahexaenoic acid) is found in the prior art, nor is the use of this formulation as an adjuvant for preserving the health of the precorneal film and/or the eye surface.

10 Claims, No Drawings

(56) References Cited

OTHER PUBLICATIONS

Quefarmacia "Snelvit: Multivitaminico [Guia De Uso y Opiniones]." QuéFarmacia, Mar. 13, 2019, Downloaded from the internet from https://translate.google.com/translate?hl=en&sl=es&u=https://quefarmacia.com/productos/snelvit/&prev=search (4 pages).

sdrugs.com. "Diabion Drug & Pharmaceuticals. Diabion Available Forms, Doses, Prices." Sdrugs.com, Oct. 19, 2018, Downloaded from the internet from https://www.sdrugs.com/?c=drug&s=diabion&ingredient=chromium%20(chromium%20polynicotinate)/folic%20acid/magnesium%20(magnesium%20oxide)/selenium%20(selenium%20yeast)/vitamin%20a%20(retinol%20palmitate)/vitamin%20b1%20(thiamine%20mononitrate)/vitamin%20b12%20(cyanocobalamin)/vitamin%20b6%20(pyridoxine%20hydrochloride)/vitamin%20c%20(ascorbic%20acid)/vitamin%20e.

Tseng, Scheffer CG, and Kazuo Tsubota. "Important concepts for treating ocular surface and tear disorders." American journal of ophthalmology 124.6 (1997): 825-835.

Yanwei, Li, Zeng Wei, and Zhu Yu. "The relationship between dry eye and lactoferrin levels in tears." Asian Biomedicine 6.1 (2012): 81-85.

Ng D et al., (2022), "An Oral Polyphenol Formulation to Modulate the Ocular Surface Inflammatory Process and to Improve the Symptomatology Associated with Dry Eye Disease," Nutrients, 14(15):3236 (15 pages).

\* cited by examiner

ORAL ADMINISTRATION FORMULATION OF BLUEBERRY EXTRACT AS A COADJUVANT FOR PRESERVING THE HEALTH OF HUMAN PRECORNEAL FILM

CROSS-REFERENCE TO RELATED APPLICATIONS

This application is a continuation under 35 U.S.C. § 371 of International Application No. PCT/MX2018/000154 filed on Dec. 18, 2018 which claims priority to Mexican National Application No. MX/a/2017/016991 filed on Dec. 20, 2017, the entire contents of which is incorporated herein by reference.

FIELD OF THE INVENTION

The present invention belongs to the field of medicine, specifically to the area of ophthalmology in which it is a formulation for oral administration to adult humans of a blueberry extract as an adjuvant for preserving the health of the precorneal tear film.

BACKGROUND OF THE INVENTION

The surface of the eyeball and the various mechanisms that maintain said surface in an optimal condition are complex. Anatomically, the eye surface comprises the epithelium of the mucous membrane in the inner portion between the upper and lower eyelids, between the margins thereof. The primary function of the eye surface is to afford clear vision, and to fulfill said function while maintaining comfort and suitable microbial flora, the eyeball surface must be covered by a stable precorneal tear film on the eye surface that is exposed to the atmosphere as mentioned in "Important concepts for treating eye surface and tear disorders," Am J Ophthalmol. 1997;124:825-835.

The relationship between the precorneal tear film and the epithelium of the eye surface is fundamental in maintaining the health of the eyeball surface as mentioned in "Important concepts for treating eye surface and tear disorders," Am J Ophthalmol. 1997;124:825-835. A stable precorneal tear film is established by hydrodynamic elements (including external factors such as the environment) and by the elements comprising said precorneal tear film. Those elements include the meibomian glands, the lacrimal glands and the epithelium of the eye surface (of the bulbar conjunctiva, the tarsal conjunctiva and the cornea).

Said elements are responsible for producing and/or maintaining the three components of healthy tears: the aqueous, lipid and mucin elements. However, even in healthy eyes, these elements are not sufficient to maintain the eye health if appropriate hydrodynamic factors are not present such as an adequate tear volume, which is controlled by healthy blinking, which produces adequate tear distribution over the entire eye surface, and is protection against desiccation through exposure to the environment. In addition, in recent years, the constant use of screens, monitors, tablets and smartphones has led to precorneal tear film disorders in healthy subjects.

These two main factors (elements that make up the precorneal tear film and hydrodynamic factors) are dependent in turn on two principal reflexes: 1) the reflex mediated by the trigeminal nerve (ophthalmic branch) and 2) the reflex mediated by the facial nerve (ophthalmic branch). This neuroanatomical integration leads to the elements that compose the precorneal tear film and the hydrodynamic factors working in harmony to produce a healthy eye surface. There are five common elements that may cause disorders in eye surface health and tear quality. A deficiency of any element composing the precorneal tear film may destabilize the eye surface, leading to conditions such as dry eye.

Said disorders are: 1) reduction in eye sensitivity due to neuropathies, 2) aqueous tear deficiency associated with glandular dysfunction, 3) precorneal tear film lipid deficiency associated with meibomian gland dysfunction, 4) tear drainage deficiency and 5) tear distribution deficiency.

In these categories, apart from the first, inflammation plays a fundamental role leading to chronic irritation and precorneal tear film conditions such as dry eye. Loss of precorneal tear film health is a multifactorial condition producing symptoms such as discomfort, a reduction in visual acuity and precorneal tear film instability. The factors involved in producing dry eye include exposure to environmental pollutants, ultraviolet (UV) rays, radiation, ozone, use of screens, tablets and smartphones, and also chronic use of topical medicines that contain preservatives (including artificial tears for treating dry eye), and medicines for treating glaucoma. These factors increase oxidative stress and inflammation of the eye surface. Synonyms for this syndrome include keratoconjunctivitis sicca, xerophthalmia, keratitis sicca, and eye surface dysfunction.

Deficiency of the aqueous layer of the precorneal tear film produces tear secretion deficiency, which results in a reduction in tear volume on the eye surface. Combined with normal tear evaporation, aqueous deficiency causes tears to become hyperosmolar. Tear hyperosmolarity causes hyperosmolarity of the eye surface cells and produces a cascade of inflammatory factors such as IL-1 alpha and IL-1 beta cytokines, tumor necrosis factor and matrix metalloproteinase (MMP-9). There are various defense mechanisms on the eye surface, including notably the presence of proteins such as lactoferrin and S100A proteins, as well as enzymes such as superoxide dismutase (SOD), peroxidase, catalase and mitochondrial oxidative enzymes.

These defense mechanisms are affected in people with loss of precorneal tear film health, a situation that favors the development of infections of the eye surface, which increases the severity of the signs and symptoms associated with this condition. Moreover, an imbalance between the level of species radicals (oxygen reagents) and the action of protective enzymes may lead to oxidative damage and to inflammation of the eye surface.

Blueberries form part of a group of foods considered "superfoods" owing to their content of natural compounds such as phenolic acids and esters, flavonoids, anthocyanins and procyanidins. Blueberry extract has anti-inflammatory, anti-oxidant and neuroprotective properties. Both anthocyanins and pterostilbene (PS) may significantly reduce the expression of anti-inflammatory mediators, tumor necrosis factor alpha (TNF-$\alpha$), interleukines (IL-1 $\beta$, IL-6, MMP-2) and metalloproteinases (MMP-9). In addition, they significantly reduce levels of oxidative stress biomarkers, malondialdehyde (MDA), 4-hydroxynonenal (4-HNE), aconitase 2 and 8-hydroxydeoxiguanosine (8-OHdG). In addition, anthocyanins and PS re-establish homeostasis between the oxygenases and the oxidative enzymes of the eye surface by reducing the expression of cyclooxygenase-2 (COX-2) and the restoration of the antioxidant activity of enzymes such as superoxide dismutase 1 (SOD1) and peroxiredoxin 4 (PRDX4) during states of hyperosmotic stress. Various publications suggest that oxidative stress states may be treated by the topical use of compounds for the relief of disorders associated with the loss of precorneal tear film health. Some suggest that L-Carnitine and pterostilbene, present in blueberry extract, may reduce levels of oxidative stress in the tissues of the eye surface.

Another cause of loss of precorneal tear film health is vitamin A deficiency. Vitamin A is liposoluble vitamin and is an essential nutrient present naturally in the precorneal tear film in healthy eyes. Vitamin A plays an important role in the production of the mucin tear layer, which is the innermost tear layer. A deficiency in vitamin A levels leads to a reduction of the mucin layer on the eye surface and to atrophy of the caliciform cells of the conjunctiva, which form that mucin layer. Topically, vitamin A protects the eye surface from free radicals of oxygen, toxins, allergens and inflammation. Vitamin A is essential for the development of the caliciform cells on the mucous surfaces and the expression of mucins of the glycocalyx. Said mucins are deficient in dry eye, which causes an unstable precorneal tear film, which is characterized by early break-up of the precorneal tear film.

Vitamin E is a liposoluble vitamin which has antioxidant effects and functions only when the lipid peroxidation chain reaction is broken. This action is crucial to stabilize the cell membranes and has been shown to prevent changes in the eye surface when there is a vitamin A deficiency. Moreover, vitamin E may regenerate other antioxidants such as ascorbic acid or glutathione. A high concentration of vitamin E, similar to that found in the AREDS formula, may enhance improvements in dry eye symptoms when taken for at least three months. Moreover, low levels of lactoferrin have been documented in the precorneal tear film of patients with dry eye. Vitamin E exists naturally as eight distinct liposoluble compounds of tocopherols and tocotrienols. Sunflower seeds and nuts, such as almonds, spinach and dark-leaved vegetables are rich sources of vitamin E.

Lactoferrin is an 82-kDa (kilodaltons) protein with a high affinity with iron, which is found in significant quantities in tears (approximately 25% of total tear proteins), and which has antimicrobial properties that enhance the activity of antibodies against particular microorganisms. Its principal action mechanism is the sequestration of free iron, which is a basic component of many pathogenic agents. Its expression has been observed in all the cells of the nasolacrimal system. Lactoferrin deficiency has been associated with keratoconjunctivitis sicca (dry eye syndrome), seborrheic meibomianitis and inflammatory eye diseases such as vernal conjunctivitis and giant papillary conjunctivitis. A publication by Jaya Devendra and Sneha Singh in the Journal of Clinical and Diagnostic Research 2015 October, Vol-9 (10) describes a randomized study of 64 patients to evaluate the function of lactoferrin administered as an oral supplement precorneal tear film deficiency in post-cataract surgery patients. The results obtained in this study establish a statistically significant difference between the time values for fluorescein break-up. On day 60, the control group had a result of 7.86 (±0.86) seconds compared with 13.9 (±0.99) seconds in the group taking oral lactoferrin, which translates as a better tear function performance on the eye surface. The small intestine in humans has receptors for absorbing lactoferrin. Said absorption is enhanced by combining lactoferrin with chitosan, which is a linear polysaccharide composed of randomly distributed chains of β-(1-4) D-glucosamine and N-acetyl-D-glucosamine. Chitosan acts as a booster for the intestinal absorption of lactoferrin, improving permeability through the mucous membranes by opening the intercellular junctions thereof.

Chitosan is derived from chitin, which is a polysaccharide found in abundance in nature, specifically in the exoskeleton of some arthropods and crustaceans. As well as using chitosan, there are ways of structurally modifying lactoferrin to improve intestinal absorption. One of these is by lactoferrin protein PEGylation, that is, the covalent attachment of polyethylene glycol (PEG) to lactoferrin. This has been shown to improve pharmacokinetics and pharmacodynamics. Nojima et al (2008) synthesized mono-PEGylated lactoferrin for the first time, which was shown to have greater resistance to pepsin proteolysis in mice.

Essential fatty acids are those fatty acids that are necessary for particular functions of the human body that said organism cannot produce and that must therefore be included in the diet. Said essential fatty acids include two polyunsaturated fatty acids: linoleic acid (omega-6) and alpha linolenic acid (ALA). Once in the body, these can be converted into eicosapentaenoic acid (EPA) and docosahexaenoic acid (DHA) also known as omega-3.

In this sense, omega-3 and omega-6 are essential fatty acids and precursors of the eicosanoids, which are hormones that act locally in the mediation of the inflammatory processes. Omega-3 molecules also promote the resolution of inflammation and regression of the tissues to their previous non-inflammatory state. Omega-3 is found in cold-water fish, including salmon, sardines and tuna, and in linseed oil. Omega-6 may be obtained from sources including soy oil, palm oil, sunflower oil, poultry, nuts and cereals.

Creuzot et al. evaluated 71 patients with mild to moderate dry eye to whom a combined nutritional supplement of omega-3 and omega-6 was administered for six months. These patients were randomized and divided against a placebo group. In the group treated with the combined supplementation there was an improvement in tear function tests such as Schirmer's test and fluorescein break-up time. These tests are objective ways of measuring tear quality and quantity. The use of a nutritional supplementation of essential fatty acids as a standard therapy for dry eye syndrome has been shown to have an anti-inflammatory effect. This effect may be the result of the synthesis of prostaglandin E3 and leukotriene B5 from EPA which inhibits the conversion of arachidonic acid to inflammatory mediators such as prostaglandin E2 and leukotriene B4 at the eyelid rim.

There are many formulations in the prior art designed as therapeutic agents for the treatment of dry eye syndrome. Said formulations may contain therapeutic concentrations of elements including essential fatty acids such as omega-3, omega-6, L-Carnitine, vitamin C, vitamin E, copper and other minerals, and also lactoferrin. However, there has been no description of a formulation designed as a food supplement which contains blueberry extract and which may be used as a coadjuvant in the maintenance of precorneal tear film health.

The invention described in document WO2004006801: "Treatment for dry eye syndrome" concerns a therapeutic formulation for use in the treatment of dry eye syndrome with a combination of omega-3 and omega-6 in combination with vitamin E, lactoferrin and other nutrients for use in people with dry eye. Said document presents an application for the use of this combination, but lacks elements for mediating the inflammation of the eye surface such as those found in blueberry extract. Moreover, this document presents the use of this formulation for the treatment of dry eye as a pharmaceutical formulation, not as a nutraceutical formulation for maintaining the precorneal tear film health based on blueberry extract.

A technology exists for the release of drugs and food supplements known as soft gel capsules, which are a suitable casing for allopathic, phytotherapeutic medicines and food supplements. Said technology provides adequate isolation ensuring suitable preservation of the active ingredients of a formulation, by maintaining low levels of oxygen in said formulation and preventing internal reactions between the different active ingredients thereof, as well as making the encased compounds easier to swallow owing to the non-stick properties thereof and offering a pleasing presentation to the consumer.

Soft gelatin is a colloidal gel, that is, a semi-solid mixture at ambient temperature that is colorless, translucent, breakable and tasteless, and is obtained from collagen derived from animal connective tissue boiled in water. Gelatin is a complex protein, that is, a polymer composed of amino acids. As with polysaccharides, the degree of polymerization, the nature of the monomers and the protein chain sequence determine its general properties. A notable property of solutions of this molecule is its behavior at different temperatures: said solutions are liquid in warm water (colloid sol) and solidify in cold water (colloidal gel). A plastifier such as glycerin or sorbitol is normally added to gelatin as an ingredient of the capsule in the final composition. The semi-liquid formulation has many advantages over solid formulations, as said semi-liquid formulations can be swallowed more easily and are an excellent vehicle for the uniform administration of the active ingredients.

In addition, the semi-liquid presentation favors much faster action of the active ingredient, as this type of formulation does not need to be previously disintegrated and dissolved in the digestive tract.

Formulations exist that contain vitamin E and various minerals in conjunction with fish oil (eicosapentaenoic acid and docohexaenoic acid) as food supplements. Some have indications in the area of ophthalmology for diseases such as age-related macular degeneration (ARMD) (AREDS formulations such as Snelvit®, Ocuvite®, Drusen® among others) and/or for people with diabetes mellitus (Diabion®, Diabitam®). However, no formulation has previously been described in the prior art for the oral administration of blueberry extract in conjunction with lactoferrin, and the combination thereof with vitamin A, vitamin E and fish oil (eicosapentaenoic acid and docohexaenoic acid) nor for its use as an adjuvant for preserving the health of the precorneal tear film.

The invention that has been developed and that will be described below is a semi-liquid formulation encapsulated in soft gelatin for oral administration to adults of a natural blueberry extract with anti-inflammatory, anti-oxidant and neuroprotective properties. Said formulation also contains elements with antimicrobial properties, essential elements that form part of a healthy precorneal tear film and fish oil which has the potential to modify the inflammatory cascade by inhibiting inflammatory mediators.

The invention that has been developed and that is described below is a formulation for oral administration to adults of blueberry extract (*Vaccinium myrtillus* L), PEGylated recombinant human lactoferrin, fish oil (eisapentaenoic acid and docohexaenoic acid), vitamin A and vitamin E which is shown in detail below.

OBJECT OF THE INVENTION

The object of this invention is to provide a nutraceutical formulation for oral administration to adults, the essential components of which are of natural origin and which uses a compound with anti-inflammatory, anti-oxidant and neuroprotective properties. It is a food supplement formulation based on blueberry extract, vitamins A and E, omega-3 and lactoferrin, among others, which may be presented in pharmaceutical form, the purpose being to increase, complement and/or supplement the ingestion thereof. It also contains elements with antimicrobial properties, essential elements that form part of the precorneal tear film and fish oil which has the potential to modify the inflammatory cascade by inhibiting inflammatory mediators, for the use of blueberry extract in humans, and all the qualities and objects that will become apparent on producing a general and detailed description of the present invention supported by the forms illustrated.

DETAILED DESCRIPTION OF THE INVENTION

The invention consists of a formulation for oral administration to adults of a natural extract of blueberry (*Vaccinium myrtillus* L), PEGylated recombinant human lactoferrin, fish oil (eicosapentaenoic acid and docohexaenoic acid), vitamin A and vitamin E. Said formulation has anti-inflammatory, anti-oxidant and neuroprotective properties. It also has antimicrobial properties, essential elements which form part of the precorneal tear film and agents with the capacity to inhibit chronic inflammation of the eye surface. The formulation has the potential to improve precorneal tear film health by improving the secretion of the aqueous component of the precorneal tear film, increasing the break-up time of the precorneal tear film, modulating the inflammatory process present in this disease and promoting the preservation of normal bacterial flora on the eye surface. The invention, which is a nutraceutical formulation, has anti-inflammatory properties provided by blueberry extract, principally owing to its high content of phenolic acids and esters, flavonoids, anthocyanins and procyanidins, as well as eicosapentaenoic and docohexaenoic acids, antimicrobials provided by lactoferrin and antioxidants produced by vitamin E. In addition, blueberry extract has antioxidant and neuroprotective functions. Both the anthocyanins and the pterostilbene (PS) may significantly reduce the expression of anti-inflammatory mediators on the eye surface such as tumor necrosis factor alpha (TNF-$\alpha$), interleukines (IL-1 $\beta$, IL-6, MMP-2) or metalloproteinases (MMP-9). In addition, said elements significantly reduce levels of oxidative stress biomarkers, malondialdehyde (MDA), 4-20 hydroxynonenal (4-HNE), aconitase-2 and 8-hydroxydeoxiguanosine (8-OHdG). Furthermore, the anthocyanins and the PS, reestablish homeostasis between the oxigenases and the oxidative enzymes of the eye surface by reducing the expression of cyclooxygenase 2 (COX2) and restoring the antioxidant activity of enzymes such as superoxide dismutase 1 (SOD1) and peroxiredoxin 4 (PRDX4) during states of hyperosmotic stress. To increase the absorption and bioavailability of the lactoferrin, PEGylated recombinant human lactoferrin may be used in this formulation, lactoferrin being thus combined with polyethylene glycol preventing structural changes in the proteins produced by the enzymes present in the gastric juices. In addition, effective use is made of the receptors present in the intestinal mucous which are specific to lactoferrin of human origin.

The source of the blueberry extract is obtained from *Vaccinium myrtillus* L. Numerous studies have demonstrated the therapeutic action of its compounds such as phenolic acids and esters, anthocyanins and procyanidins. The anti-inflammatory action of this formulation is provided by the blueberry extract and by the inflammation modulating action of the omega-3 component contained in the fish oil. Omega-3 is a substrate for the synthesis of prostaglandin E3 and leukotriene B5 which inhibits the conversion of arachidonic acid to inflammatory mediators at the eyelid rim. The basic reason for using omega-3 as an oral supplement in the treatment of meibomian gland dysfunction may be explained by two different action mechanisms. The decomposition of omega-3 fatty acids results in the creation of anti-inflammatory molecules that suppress the inflammatory pathways found in meibomian gland dysfunction. Moreover, the unstable precorneal tear film associated with meibomian gland dysfunction is the cause of the deficiency in precorneal tear film health. Furthermore, supplementation with omega-3 fatty acids changes the fatty acid composition of the meibomian gland producing a secretion that contains increased levels of unsaturated fatty acids which are in a liquid state at body temperature, thus preventing the ducts of the meibomian glands from being blocked and the consequent inflammation.

The antimicrobial action is provided by the iron sequestering action of lactoferrin. Iron is an essential element for the metabolism of many pathogenic agents. In addition, the absence of lactoferrin in the tears is associated with dry eye symptomology and it is therefore thought that oral supplementation which improves concentrations of lactoferrin would have positive effects on dry eye disease as mentioned by Lin Yanwei et al in "The relationship between dry eye and lactoferrin level in tears," Asian Biomedicine vol.6, No.1 February 2012.)

Vitamin A and vitamin E enhance tear adhesion to the eye surface by promoting the production of the mucin layer produced by the caliciform cells in the conjunctiva. Moreover, vitamin A is an essential component of the precorneal tear film. Both have antioxidant activity.

The description in the preceding paragraphs, the anti-inflammatory effect and precorneal tear film stabilization of blueberry extract in combination with supplementation with lactoferrin, vitamin A, vitamin E and the addition of essential omega-3 fatty acids from fish oil produce a formulation that regulates the inflammatory processes associated with the loss of health of the eye surface and of the precorneal tear film. This formulation is therefore a food supplement of which the main nutraceutical component is blueberry extract as an adjuvant to preserve precorneal tear film health. Based on the above, a formulation was produced for oral administration to adults of natural blueberry extract presented for human oral consumption which contains:

Blueberry extract (*Vaccinium myrtillus* L): 100 mg
Eicosapentaenoic acid (EPA) equivalent to 9,000 to 12,000 mg
Docosahexaenoic acid (DHA) equivalent to 6,000 to 8,000 mg
Recombinant human lactoferrin which could be combined with polyethylene glycol (PEGylation) or combined with chitosan equivalent to 350 mg.
Vitamin E: 15 mg (400 UI)
Vitamin A: 1,500 UI
The excipient may contain a surfactant agent.

The formulation may be presented in pharmaceutical form as a non-food matrix such as a tablet, pill, capsule, powder, granules, syrup, elixir, suspension or solution. Ideally, to enhance consumption it may be encapsulated in a colloidal gel (soft gelatin), which reduces unpleasant odors and flavors. The above formulation allows suitable consumption of the ingredients in the digestive tract.

The formulation for oral administration to adults of natural blueberry extract in combination with lactoferrin, vitamin A, vitamin E and fish oil (eicosapentaenoic acid and docohexaenoic acid) presented for human oral consumption, providing for the first time a formula of this type in the area of ophthalmology. It should be stated that the above formulation may contain other compounds to improve the anti-inflammatory and antioxidant properties thereof.

Until now there has been no substance that did not have undesirable side effects and therefore to reduce the risk of presentation of said reactions, said formulation should be used as suggested (once a day). It may also be used to maintain the health of the precorneal tear film and of the eye surface.

The invention has been disclosed sufficiently for a person skilled in the art to be able to reproduce and obtain the results described therein. However, a person skilled in the art responsible for the present invention may be able to make modifications not described in the present application, and therefore if the subject matter claimed in the following claims is required for the application of said modifications to a particular structure or in the manufacturing process thereof, said structures shall be comprised within the scope of the invention.

We claim:

1. A method to improve the health of precorneal tear film of the patient in need thereof, comprising the steps of:
    orally administering to the patient a food supplement formulation comprising:
        a. blueberry extract;
        b. eicosapentaenoic acid (EPA) omega;
        c. docosahexaenoic acid (DHA) omega-3;
        d. recombinant human lactoferrin covalently bound directly to one or more polyethylene glycol moieties;
        e. Vitamin E;
        f. Vitamin A; and
        g. an excipient;
    wherein said food supplement formulation is an adjuvant;
    wherein said excipient is a surfactant that promotes the formation of micelles; and
    wherein said food supplement formulation is encapsulated with a colloidal gel that is soft gelatin.

2. The method according to claim 1, wherein the amount of blueberry extract in the food supplement formulation is between 10 mg and 1,000 mg.

3. The method according to claim 1, wherein the amount of eicosapentaenoic acid (EPA) omega-6 in the food supplement formulation is between 9,000 mg and 12,000 mg.

4. The method according to claim 1, wherein the amount of docosahexaenoic acid (DHA) omega-3 in the food supplement formulation is between 6,000 mg and 8,000 mg.

5. The method according to claim 1, wherein the amount of recombinant human lactoferrin in the food supplement formulation is between 100 mg and 500 mg.

6. The method according to claim 5, wherein the recombinant human lactoferrin in the food supplement formulation is modified with polyethylene glycol, chitosan or a combination thereof.

7. The method according to claim 1, wherein the amount of Vitamin E in the food supplement formulation is 100 UI (unidad internation or international unit) to 400 UI (unidad internation or international unit).

8. The method according to claim 1, wherein the amount of Vitamin A in the food supplement formulation is 500 UI (unidad internation or international unit) to 1,500 UI (unidad internation or international unit).

9. The method according to claim 1, wherein the food supplement weighs approximately 100 g.

10. The method according to claim 1, wherein said blueberry extract is selected from the *Vaccinium myrtillus* L species.

* * * * *